US008828715B2

(12) United States Patent
Pant et al.

(10) Patent No.: US 8,828,715 B2
(45) Date of Patent: Sep. 9, 2014

(54) PARTICLE ADHESION ASSAY FOR MICROFLUIDIC BIFURCATIONS

(75) Inventors: Kapil Pant, Huntsville, AL (US); Balabhaskar Prabhakarpandian, Madison, AL (US); Shivshankar Sundaram, Madison, AL (US); Angela I. Rea-Ramsey, Madison, AL (US)

(73) Assignee: CFD Research Corporation, Huntsville, AL (US)

(*) Notice: Subject to any disclaimer, the term of this patent is extended or adjusted under 35 U.S.C. 154(b) by 1018 days.

(21) Appl. No.: 12/399,606

(22) Filed: Mar. 6, 2009

(65) Prior Publication Data

US 2010/0227312 A1 Sep. 9, 2010

(51) Int. Cl.

| | |
|---|---|
| ***C12M 1/34*** | (2006.01) |
| ***C12M 3/00*** | (2006.01) |
| ***B01L 3/00*** | (2006.01) |

(52) U.S. Cl.

CPC ....... *B01L 3/5027* (2013.01); *B01L 2300/0864* (2013.01); *B01L 2300/0867* (2013.01); *B01L 2400/086* (2013.01); *B01L 3/502761* (2013.01)

USPC .................. 435/287.9; 435/283.1; 435/287.2; 435/287.1; 435/288.5

(58) Field of Classification Search

CPC ............ B01L 3/5027; B01L 3/502761; B01L 2400/086; B01L 2300/0867; B01L 2300/0864

USPC ........... 435/283.1, 287.2, 287.1, 287.9, 288.5

See application file for complete search history.

(56) References Cited

U.S. PATENT DOCUMENTS

| | | | | |
|---|---|---|---|---|
| 6,432,630 | B1 * | 8/2002 | Blankenstein | 435/4 |
| 7,371,400 | B2 | 5/2008 | Borenstein et al. | 424/423 |
| 7,419,822 | B2 | 9/2008 | Jeon et al. | 435/288.5 |
| 8,372,629 | B2 * | 2/2013 | Southern et al. | 435/288.3 |
| 2002/0037499 | A1 * | 3/2002 | Quake et al. | 435/5 |
| 2003/0190608 | A1 * | 10/2003 | Blackburn | 435/6 |
| 2006/0173394 | A1 | 8/2006 | Stroock et al. | 602/41 |
| 2007/0006926 | A1 | 1/2007 | Prakash et al. | 137/800 |
| 2007/0172389 | A1 * | 7/2007 | Wilding et al. | 422/58 |

FOREIGN PATENT DOCUMENTS

| | | | |
|---|---|---|---|
| WO | WO 2004/059299 A1 | 7/2004 | G01N 21/00 |
| WO | WO 2008/055915 A2 | 5/2008 | |
| WO | WO 2008/098179 A1 | 8/2008 | G01N 1/20 |

OTHER PUBLICATIONS

Prabhakarpandian et al., Synthetic microvascular networks for quantitative analysis of particle adhesion, Mar. 2008, Biomed Microdevices, 10: pp. 585-595.*

Yang et al., A microfluidic device for continuous, real time blood plasma separation, 2006, Lab Chip, 6: pp. 871-880.*

* cited by examiner

*Primary Examiner* — Melanie Y Brown

(74) *Attorney, Agent, or Firm* — Maschoff Brennan, PLLC

(57) ABSTRACT

A method for characterizing particle adhesion in microfluidic bifurcations and junctions comprises at least one idealized bifurcation or junction. Multiple bifurcations and/or junctions can be combined on a single microfluidic chip to create microfluidic networks configured for assays specifically to characterize particle interactions at junctions or to screen particles for desired interactions with microfluidic bifurcations and/or junctions.

20 Claims, 11 Drawing Sheets

Serial and Parallel Arrangement of Bifurcations and Junctions

Symmetric Diameter, Symmetric Angle

Symmetric Diameter, Asymmetric Angle

Asymmetric Diameter, Symmetric Angle

Asymmetric Diameter, Asymmetric Angle

Serial Arrangement of Bifurcations and Junctions

Serial Arrangement of Bifurcations and Junctions

Parallel Arrangement of Bifurcations and Junctions

Serial and Parallel Arrangement of Bifurcations and Junctions

Serial and Parallel Arrangement of Bifurcations and Junctions

Serial and Parallel Arrangement of Bifurcations and Junctions

PARTICLE ADHESION ASSAY FOR MICROFLUIDIC BIFURCATIONS

STATEMENT REGARDING FEDERALLY SPONSORED RESEARCH OR DEVELOPMENT

The U.S. Government may have certain rights in this invention pursuant to SBIR Contract Number 1R43HL076034-01A1 awarded by the National Institutes of Health.

CROSS-REFERENCE TO RELATED APPLICATIONS

Not Applicable

BACKGROUND OF THE INVENTION

1. Field of the Invention

The present invention pertains to microfluidic devices and particle adhesion in biological microcirculation. In particular, the invention is a method for characterizing particle adhesion properties in idealized synthetic microvascular bifurcations and junctions and to predict particle adhesion dynamics in biological microcirculation.

2. Description of Related Art

A considerable body of work has been developed regarding in-vitro systems for the study of vascular endothelial responses, leukocyte adhesion, and drug carrier delivery in the microcirculation of capillary beds. For example, in-vitro flow chambers have facilitated the identification of biological molecules involved in the adhesion of leukocytes to the endothelium. These results have led in part to an effort to understand endothelial cell-leukocyte interactions using carefully controlled in-vitro flow cell experiments.

The adhesion of particles such as leukocytes, platelets, liposomes/lipisomes, and microencapsulated drug carriers to microvascular endothelium is influenced by the geometric features of the vasculature, local hemodynamics, and numerous receptor-ligand interactions between endothelial cells and particles. Local hemodynamic factors associated with microvascular geometry such as wall shear stress, pressure, and residence time influence the rates, amounts, and distributions of particle adhesion as well as endothelial cell morphology and function. This complex interplay between flow, cells, and particles is still poorly understood and it is not possible to predict, for example, adhesion patterns and numbers of adhered particles in the microvasculature based on current in-vitro flow cell technologies.

The present invention is based, in part, on the finding by the inventors that microfluidic surfaces at bifurcations and junctions in biological and synthetic microvascular networks interact with particles moving through them to an unexpected degree. The inventors have found that interactions of particles at synthetic bifurcations are predictive of and correlate with particle interactions in physiological bifurcations. This surprising finding indicates that simple, idealized bifurcations, junctions, and combinations thereof, fabricated using known technologies can be used, for example, to screen for particle and cell adhesion at corresponding structures in biological microvascular networks. Methods of the present invention can be used to screen particles and cells for the presence of desired or absence of undesirable interactions with the surfaces of biological microvascular structures such as bifurcations and junctions.

BRIEF SUMMARY OF THE INVENTION

In one aspect, the present invention is an in-vitro method for characterizing one or more interactions of particles with one or more microfluidic bifurcations and/or junctions.

In another aspect, the present invention is an in-vitro assay method for quantifying one or more interactions between particles and one or more microfluidic bifurcations and/or junctions.

In yet another aspect, the present invention is an in-vitro method for screening particles for one or more interactions with one or more microfluidic bifurcations and/or junctions.

In yet another aspect, the present invention is an in-vitro method and microfluidic chip for characterizing one or more interactions between particles and microfluidic surfaces within a microfluidic network.

DEFINITIONS

As used herein, the term “idealized” in association with a microfluidic network, junction, or bifurcation is used to describe a synthetic network, junction, or bifurcation consisting of straight microfluidic channels joined at acute, right, or obtuse angles.

A “microfluidic chip” is constructed using well known techniques employed in the semiconductor industry such as photolithography, wet chemical etching, thin film deposition and soft lithography using polymeric substrates, such as Polydimethylsiloxane (PDMS). This is in contrast to microfluidic systems formed in gels made of proteins, chitosan, proteoglycans, and/or other extracellular matrix components. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

As used herein, a microfluidic channel is preferably rectangular or circular or semi-circular in cross-section. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

As used herein, the word "bifurcation" is meant to include a parent channel splitting into two or more daughter channels. The channels comprising a bifurcation have walls made of a manufactured substrate and may be coated with biological molecules and/or cells. It is further understood that in a general context, a "bifurcation" may also be a junction, which has the same structure as a bifurcation but in which fluid flows in the opposite direction from the daughter channels into the parent channel.

DETAILED DESCRIPTION OF THE INVENTION

Figure 1:
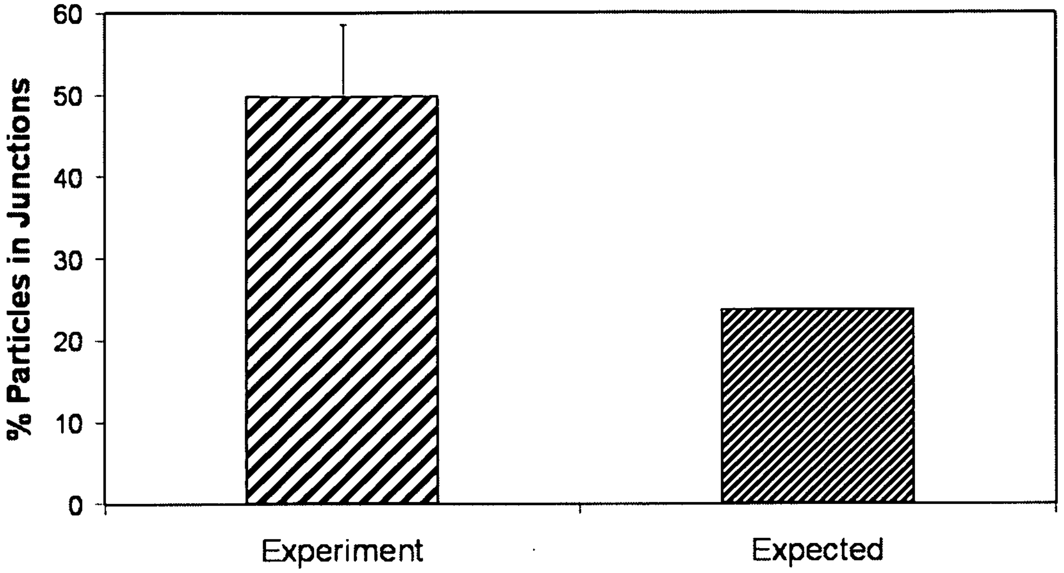
FIG. 1 is a graph showing the ratio of particle adhesion to a junction vs. overall adhesion in a synthetic microvascular network. The experimentally observed percentage of particles adhering in the junction is significantly larger than the expected value, based upon uniform adhesion in the network.

The present invention is based, in part, on the inventors' discovery of an unexpectedly high correlation between micro-scale vessel junctions and the rate and extent of particle adhesion to micro-vessel walls (FIG. 1). For particles moving through physiological and synthetic microfluidic networks, the ratio of adhesion to junction walls vs. straight walls is in excess of 2:1.

Figure 2:
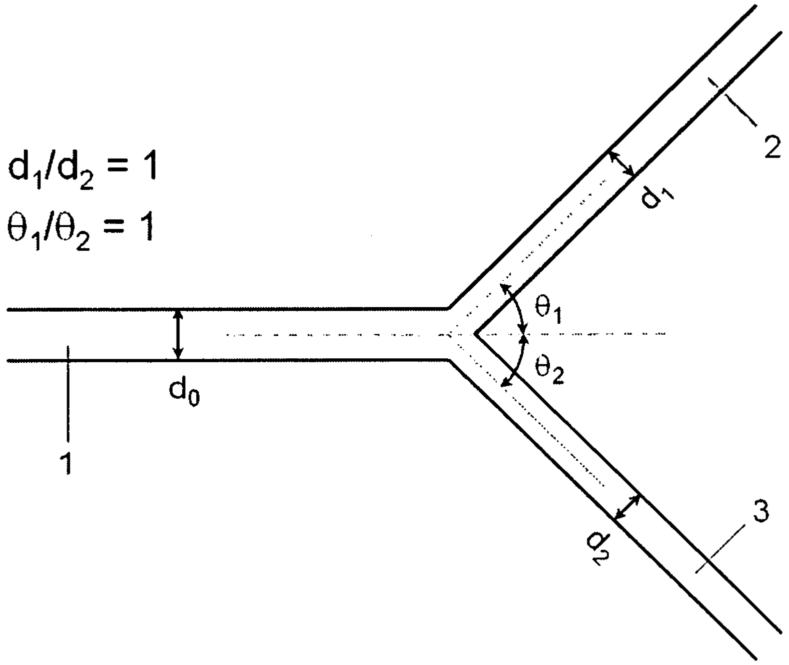
FIG. 2 shows a symmetric bifurcation with symmetric daughter diameters.

The simplest embodiment of the present invention involves the use of a single idealized junction or bifurcation in which fluid flow converges or diverges, respectively. FIG. 2 shows the basic elements of an idealized bifurcation having an inlet leading into parent channel and two daughter channels of equal diameters or cross section that diverge from the line of the parent channel in a symmetrical manner and leading to two outlets. The same structure with reversed flow having two inlets and one outlet would form an equivalent junction.

The idealized bifurcations and junctions used in the present invention consist of linear parent and daughter channels having rectangular or circular or semi-circular cross-sections that diverge or converge at angles of between 15 degrees and 135 degrees. The diameters or cross-sections of the channels are between 10 and 500 micrometers. The bifurcations and junctions are categorized as illustrated in FIG. 2 through FIG. 5. In the figures, $d_0$, $d_1$, and $d_2$ represent the diameters of the parent and first and second daughter channels, respectively. $\theta_1$, and $\theta_2$ represent the angles formed between the parent channel and the first and second daughter channels, respectively.

FIG. 2 shows the structure of a symmetric bifurcation with symmetric daughter diameters. In this case, the parent branch 1 splits into two daughter branches 2 and 3 such that the diameter of daughter 2 is the same as the diameter of daughter 3. The angle between the parent 1 and daughter 2 is identical to the angle between parent 1 and daughter 3.

Figure 3:
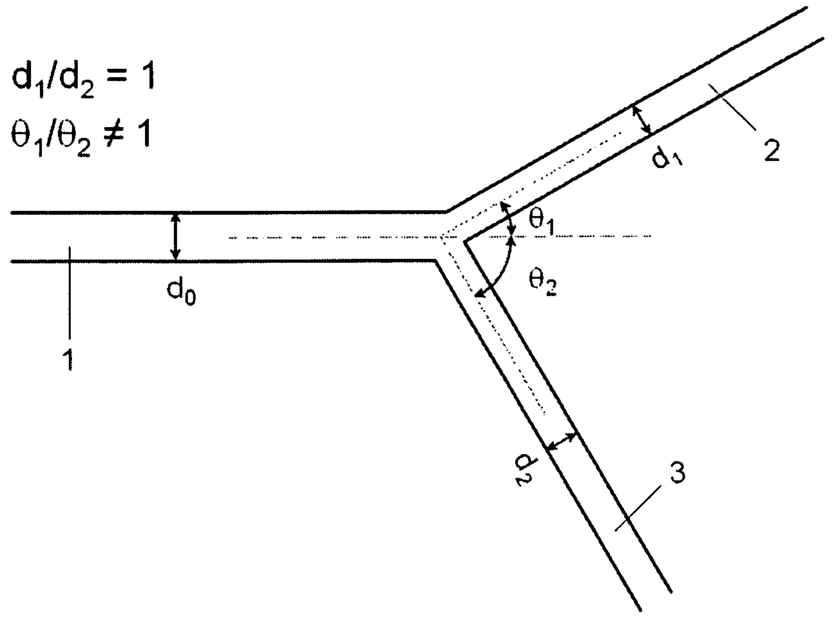
FIG. 3 shows an asymmetric bifurcation with symmetric daughter diameters.

FIG. 3 shows the structure of an asymmetric bifurcation with symmetric daughter cross-sectional areas (width×depth for channels having a rectangular cross-section, and diameter×π for channels having circular cross-sections, and diameter/2×π for channels having semi-circular cross-sections). In this case, the parent branch 1 splits into two daughter branches 2 and 3 such that the diameter of daughter 2 is the same as the diameter of daughter 3. The angle between the parent 1 and daughter 2 is different from the angle between parent 1 and daughter 3.

Figure 4:
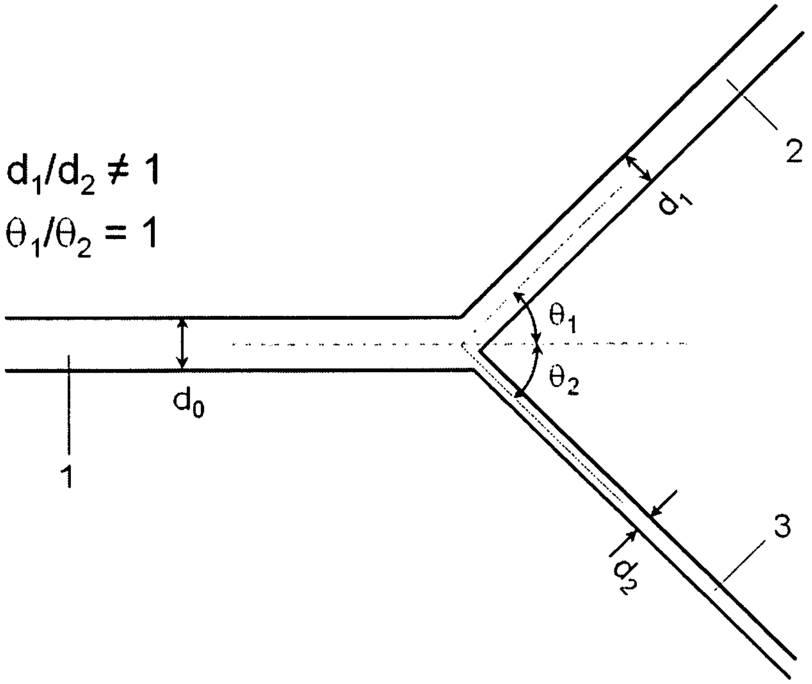
FIG. 4 shows a symmetric bifurcation with asymmetric daughter diameters.

FIG. 4 shows the structure of a symmetric bifurcation with asymmetric daughter diameters. In this case, the parent branch 1 splits into two daughter branches 2 and 3 such that the diameter of daughter 2 is different from the diameter of daughter 3. The angle between the parent 1 and daughter 2 is identical to the angle parent 1 and daughter 3.

Figure 5:
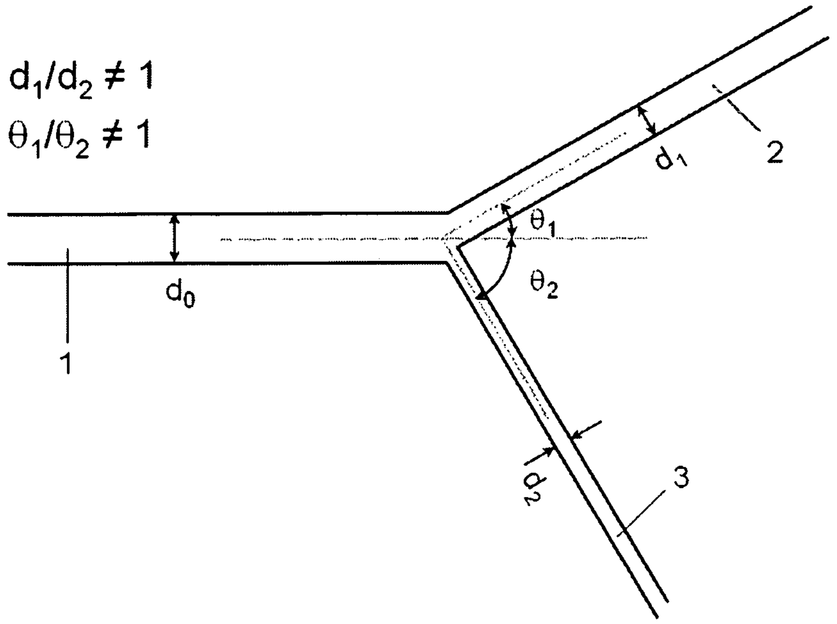
FIG. 5 shows an asymmetric bifurcation with asymmetric daughter diameters.

FIG. 5 shows the structure of an asymmetric bifurcation with asymmetric daughter diameters. In this case, the parent branch 1 splits into two daughter branches 2 and 3 such that the diameter of daughter 2 is different from the diameter of daughter 3 and the angle between the parent 1 and daughter 2 is different from the angle parent 1 and daughter 3.

Figure 6:
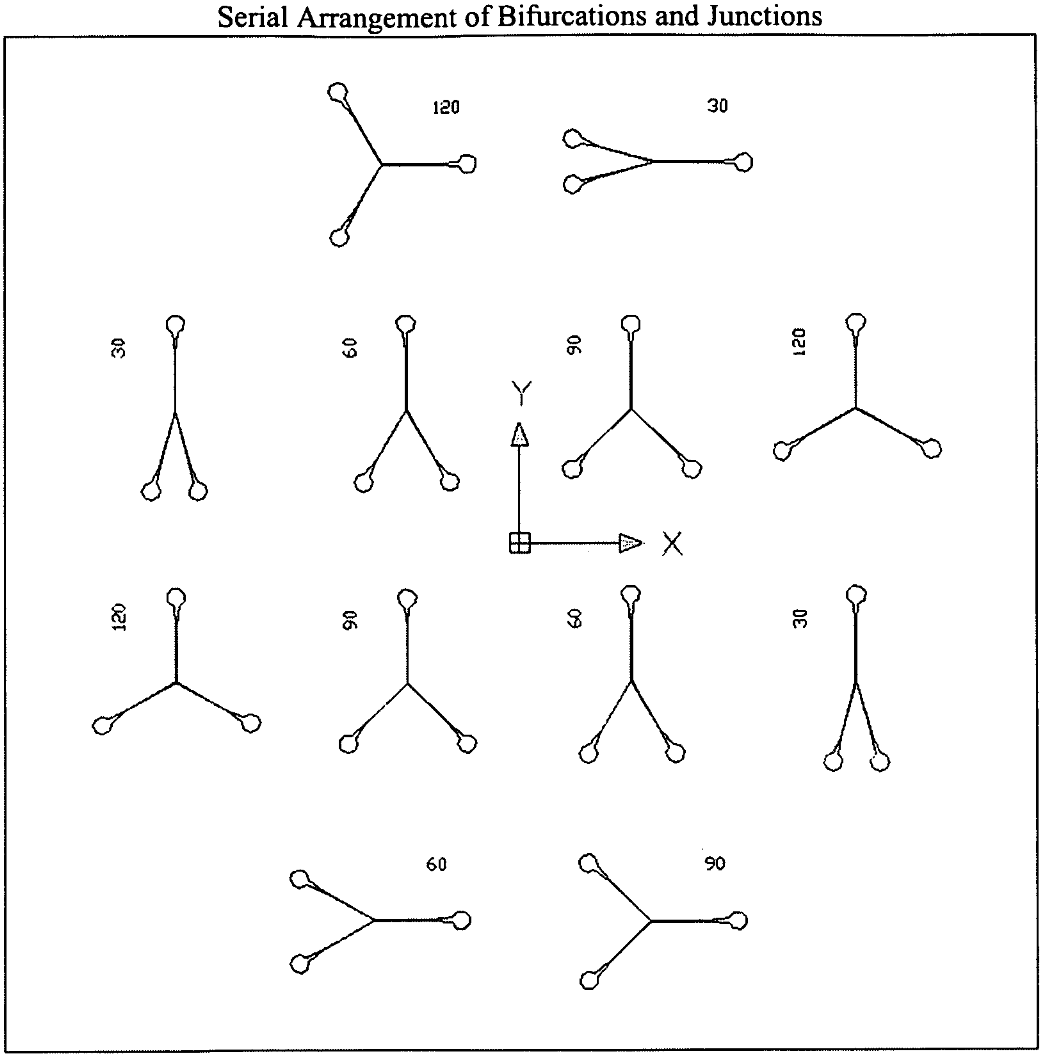
FIG. 6 is a drawing of a microfluidic chip comprising a plurality of symmetric microfluidic bifurcations with 30°, 60°, 90°, and 120° angles configured sequentially for particle and cellular adhesion assays.
Figure 7:
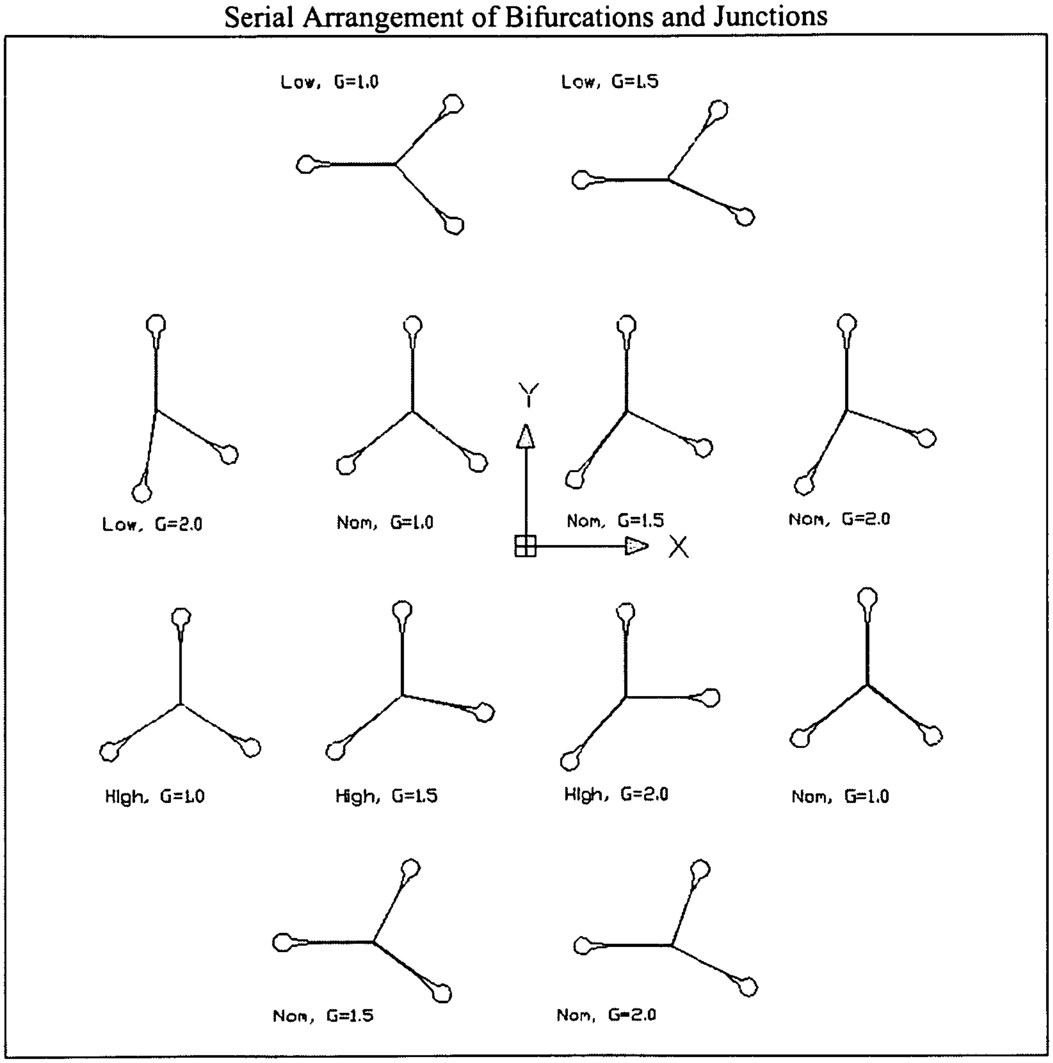
FIG. 7 is a drawing of a microfluidic chip comprising a plurality of asymmetric microfluidic bifurcations with low, nominal, and high contained angles wherein low refers to the smallest contained angle and high refers to the largest contained angle.

The method of the present invention may employ a single idealized bifurcation or junction or, more preferably, the serial or simultaneous use of plurality of junctions and/or bifurcations. FIG. 6 and FIG. 7 illustrate single microfluidic chips, each comprising a plurality of microfluidic bifurcations/junctions arranged for simultaneous use or in a serial fashion, one after another. FIG. 6 shows a microfluidic chip comprising a plurality of symmetric bifurcations with different contained angles (30°, 60°, 90°, and 120°) used sequentially to implement a particle adhesion assay. FIG. 7 shows a microfluidic chip comprising a plurality of asymmetric bifurcations with Low, Nom, and High contained angles, wherein Low refers to the smallest contained angle, and High refers to the largest contained angle. The degree of angle asymmetry is indicated by G=1, G=1.5, and G=2.0, where increasing G values indicate increasing asymmetry in the bifurcation and the bifurcations are used sequentially to implement a particle and cellular adhesion assay.

Figure 8:
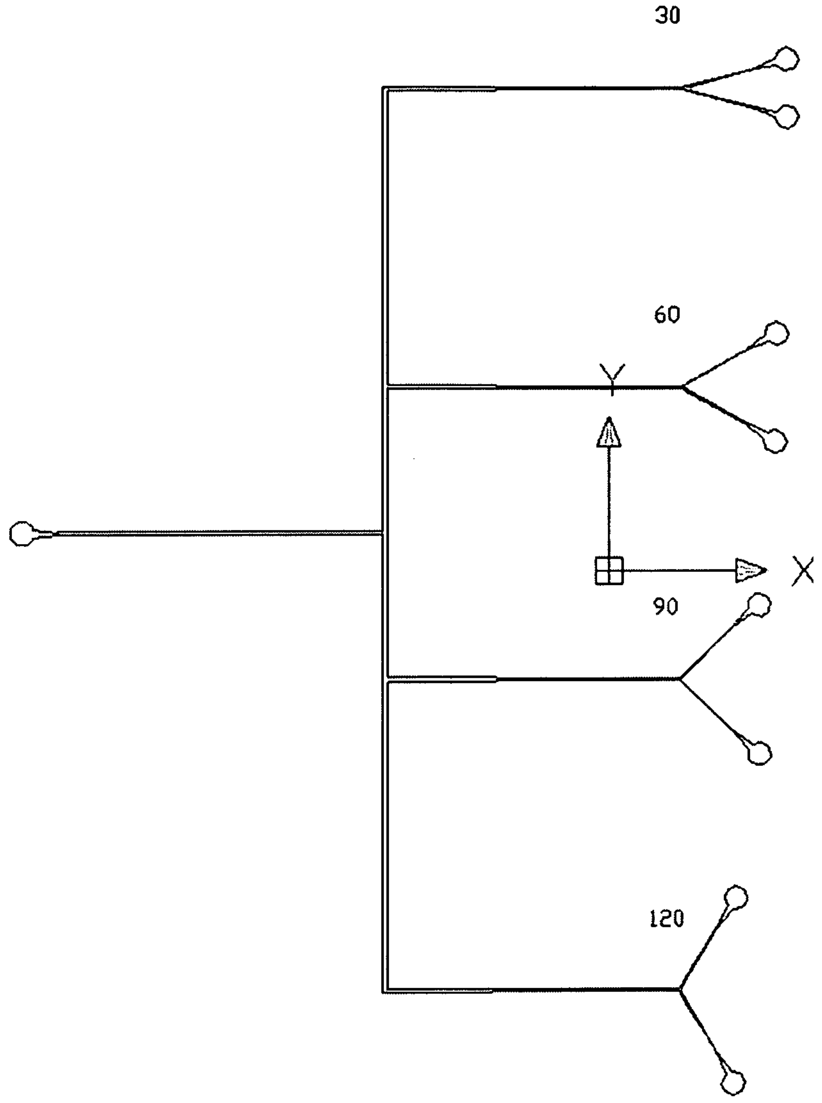
FIG. 8 is a drawing of a single microfluidic chip comprising a plurality of bifurcations arranged in parallel.

The method of the present invention may also employ a plurality of idealized bifurcations or junctions arranged in parallel or in series. FIG. 8 illustrates a single microfluidic chip comprising a plurality of bifurcations arranged in parallel.

Figure 9:
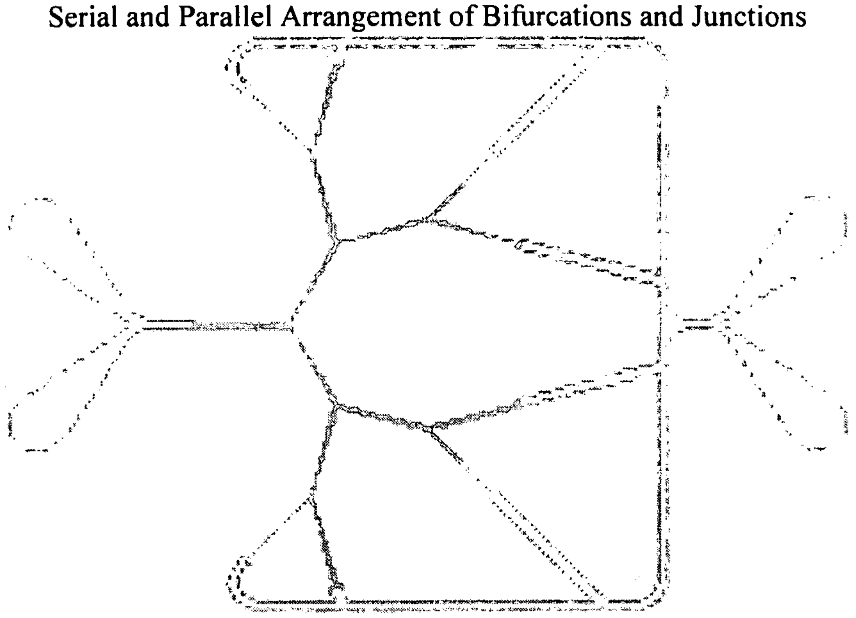
FIG. 9 is a drawing of an idealized microfluidic network comprising a plurality of bifurcations in which no contained angle is repeated and the lengths of the individual branches are maintained constant throughout the network.
Figure 10:
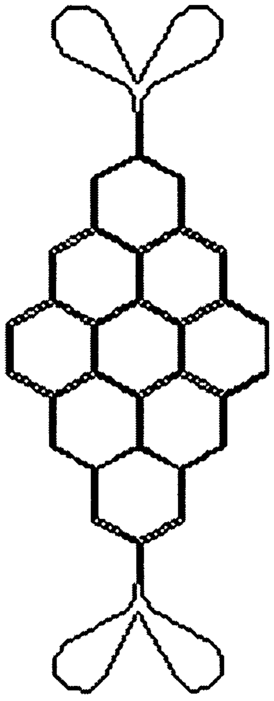
FIG. 10 is a drawing of an idealized microfluidic network comprising a plurality of identical, symmetric bifurcations and junctions.
Figure 11:
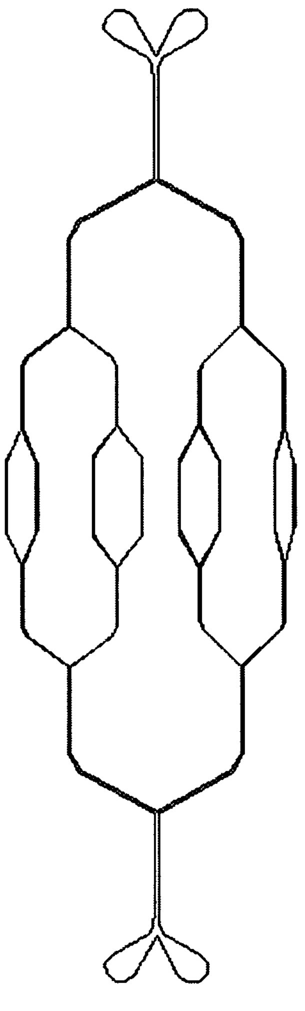
FIG. 11 is a drawing of an idealized microfluidic network comprising a plurality of bifurcations and junctions in which no bifurcation or junction geometry is repeated.

The method of the present invention may also employ a plurality of idealized bifurcations and junctions arranged to form an idealized microfluidic network. FIG. 9 illustrates a single microfluidic chip comprising a plurality of bifurcations in which no contained angle is repeated and the lengths of the individual branches are maintained constant throughout the network. FIG. 10 illustrates an idealized microfluidic network comprising a plurality of identical, symmetric bifurcations and junctions. FIG. 11 illustrates an idealized microfluidic network comprising a plurality of bifurcations and junctions in which no bifurcation or junction geometry is repeated. The present method may also employ one or a plurality of junctions/bifurcations with more than three channels.

The idealized bifurcations, junctions, and networks of the present invention are preferably made from polydimethylsiloxane (PDMS) using polymeric microfluidic technology but may be made using any one of a variety of techniques commonly used in semiconductor or microfluidic technologies. PDMS offers the advantages of gas permeability beneficial for cell culture, optical transparency, ease of casting, and producing small volume, inexpensive, disposable chips. Very thin (<100 μm) PDMS constructs can be successfully used to for long-term cell culture and cellular assays on microfluidic chips. By bonding the polymer microchannel on to a custom glass bottom laid out in the appropriate form, microfluidic chips may be formed onto standard 24 or 96 well plates, providing for scale-up and high-throughput screening.

Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques.

The channels forming the bifurcations/junctions may be coated with native or recombinant with proteins, glycoproteins, proteoglycans, or other substrate molecules to assay for associations with particles or to facilitate the growth of cells on the inner surfaces of the channels. Examples of substrate molecules include collagen, gelatin, laminin, and fibronectin. The channels may also be coated with adhesion molecules such as P-selectin, E-selectin, ICAM-1, or other receptors to facilitate adhesion of specific cell types or particles such as lipisomes or drug encapsulating or targeting agents.

General methods for coating many plastics with proteins and other molecules are known in the art and may be adapted for coating idealized bifurcations, junctions, and networks.

Example

Coating with Recombinant Fibronectin

A 500 ul-1 ml syringe filled with 200-300 ul fibronectin solution is connected to the inlet port of a microfluidic network chip. A pump is used to force the fibronectin solution from the syringe at a flow rate of 10 ul/min until fibronectin solution comes out of the outlet port. Following this, the flow rate is reduced to 1 ul/min for 10 min or 10 ul/min for 10 minutes, depending on the chip dimensions. The chip is then kept overnight at room temperature in a sterile environment or at 4° C. overnight in a humidified chamber.

Channels forming the bifurcations, junctions, or networks of the present invention may be coated with cultured cells and used to assay for or otherwise characterize the adhesion or uptake of particles by the cells. Examples of cells that may be cultured within the channels of the present invention include both primary cells and immortalized cell lines. Primary cells include cells freshly harvested from animals and donors that cannot survive beyond 10 passages in in-vitro conditions (e.g. endothelial cells, epithelial cells, fibroblasts smooth muscle cells, etc.) Immortalized cell lines include cells that can be cultured indefinitely in in-vitro conditions (e.g. cancer cell lines, neural cell lines, etc.). Virtually any cell type can be cultured within the channels, depending on the adhesion process being studied. For example, one may screen for cancer targeting molecules in a realistic environment using channels coated with the tumor cells being targeted. Libraries of microencapsulated drugs comprising variable targeting molecules can be screened using bifurcations, junctions, or networks coated with the target tumor cells. The cell cultures used may also comprise co-cultures comprising combinations of cells.

The idealized bifurcations, junctions, and networks of the present invention may be used to assay or screen for or to characterize particle interactions including particle adhesion to one or more proteins or cells types and uptake into cells at or near bifurcations and junctions.

Example

Adhesion Assay on Channels Coated with Proteins

A suspension of particles, such as polystyrene beads, of desired size are coated with antibodies that bind to a protein coating a network of bifurcations and junctions. A drop of PBS solution is applied to each of the port openings and the chip is mounted on an automated microscope stage. Desired experimental areas (e.g. complete chip or selected locations) are then programmed into a stage movement controller and stored. Key locations include the middle of the parent and daughter branches and the bifurcations or junctions. The particle suspension, at concentrations ranging from $5\times10^3$/ml to $1\times10^7$/ml is loaded into a 1 ml syringe and mounted on a syringe pump. Two tubes primed with PBS are connected to the outlet ports and immersed in a tube filled with PBS to maintain pressure. The syringe pump is turned on at a flow rate of 10 ul/min to prime the tubing. Once the tubing is primed, the flow rate is reduced in a stepwise manner to an inlet shear rate corresponding of 500 sec-1. The tubing is then inserted into the inlet port of the chip. Shears are then held constant for 3 minutes for each of the shear conditions varying from 500 sec-1 to 7.5 sec-1 in the same chip in a decreasing order. Alternatively, the experiment can be performed with each shear held constant for 10 minutes. Every 3 minutes, an image is taken of the entire chip or of selected locations selected using an automated stitching procedure. The images are post-processed with specific Areas of Interest (AOIs) ranging from μm to mm size, depending on chip and channel dimensions, to yield the counts of particles adhered at each of the selected locations. A plot of shear vs. particles bound per unit area is plotted for each of the locations to yield a shear-adhesion map.

Example

Adhesion Assay on Channels Coated with Cultured Cells

A cell culture matrix comprising gelatin and fibronectin is injected into the channels of a network along with the desired cell culture medium at a flow rate of 10 ul/min for 10 min. The network chip is then kept in a cell culture incubator for 2-4 hours. Cells at concentrations ranging from $1\times10^3$/ml to $1\times10^7$/ml are introduced into the chip using a syringe pump. The cells are continuously perfused with media at shear rates of 7.5-120 sec-1 until they are 80% confluent. The cells are then activated with cytokines (e.g., TNF-alpha, IL-1beta) for a selected duration (e.g., 4 hr, 24 hr). Desired experimental areas are then programmed into the stage movement controller of an automated microscope stage and stored. Key locations include the middle of the parent and daughter branches and the bifurcations or junctions.

Particles in concentrations ranging from $5\times10^3$/ml to $1\times10^7$/ml coated with antibodies to corresponding upregulated adhesion molecules (e.g, E-Selectin, ICAM-1 on endothelial cells) are injected into the channels at decreasing shear rates of from 500 sec-1 to 7.5 sec-1. Every 3 minutes, an image is taken of the entire chip or of key locations using an automated stitching procedure. The images are post-processed with specific AOIs ranging from μm to mm size to yield the counts of particles adhered at each of the selected locations. A plot of shear vs. particles bound per unit area is plotted for each of the locations to yield a shear-adhesion map.

Example

Particle Uptake Study on Channels Coated with Cultured Cells

A cell culture matrix comprising gelatin and fibronectin is injected into an idealized bifurcation along with the desired cell culture medium at a flow rate of 10 ul/min for 10 min. The network chip is then kept in a cell culture incubator for 2-4 hours. Cells at concentrations ranging from $1\times10^3$/ml to $1\times10^7$/ml are introduced into the chip using the syringe pump. The cells are continuously perfused with media at shear rates of <15 sec-1 until they are 80% confluent. Desired experimental areas are then programmed into the stage movement and stored. Key locations include the middle of the parent channel, the junction and the middle of each of the two daughter channels. Particles in concentrations ranging from $5\times10^3$/ml to $1\times10^7$/ml encapsulating drugs/genes (e.g. luciferase, GFP), fluorescent tags (rhodmaine, FITC) or nanopolymers complexated with tagged drug are injected into the inlet channel at decreasing at shear rates ranging from 500 sec-1 to 7.5 sec-1. The particle solution can be flowed through in a loop or in a single pass fashion using a peristaltic pump or a syringe pump. Each shear rate experiment is performed on a new chip. Every 4 hours, an image is taken of the entire chip or of the key locations using an automated stitching procedure. The images are post-processed with specific ROI's ranging from μm to mm size to yield % of cells with uptaken particles. A plot of shear vs. % of cells (at each location) expressing uptaken moities is then calculated.

What is claimed is:

1. A method for characterizing one or more interactions between particles and an idealized microfluidic bifurcation comprising the steps of:

introducing a liquid suspension of particles into an inlet of a microfluidic chip comprising an inlet and an outlet in fluid communication with an idealized microfluidic bifurcation wherein the microfluidic chip includes:

the idealized microfluidic bifurcation being a joint that fluidly couples a parent channel and two or more daughter channels, one or more locations of interest that include the idealized microfluidic bifurcation having a wall with a coating;

the depth and width of each of the parent channel and daughter channels is between 10 micrometers and 500 micrometers, and the daughter channels each form an angle of between 15 degrees and 135 degrees at the idealized microfluidic bifurcation with respect to the parent channel;

causing the particle suspension to flow from the inlet through the idealized microfluidic bifurcation to the outlet such that at least a portion of the particles interact with the coating at the idealized microfluidic bifurcation;

measuring the particles that interact with the coating at the one or more locations of interest;

determining the distribution of particles on the coating at the one or more locations of interest with respect to the idealized microfluidic bifurcation; and correlating the distribution of particles with one or more interactions between the particles and the coating of the idealized microfluidic bifurcation.

2. The method of claim 1, wherein the coating includes a substance selected from the group consisting of substrate molecules, biological macromolecules, cells, and combinations thereof and the one or more interactions correlated with the distribution of particles includes an interaction between the particles and the substance.

3. The method of claim 1, wherein the particles are selected from the group consisting of cells, liposomes, lipisomes, lipoproteins, microencapsulated drugs, particulate drug carriers, nanoparticles, microparticles, polymer beads, viruses, spores and combinations thereof.

4. The method of claim 1, wherein the particles are flowed in the idealized microfluidic bifurcation using a flow scheme selected from the group consisting of single pass, multiple pass, and recirculating loop.

5. The method of claim 1, wherein the one or more interactions between the particles and the coating of the idealized microfluidic bifurcation is selected from the group consisting of: particle adhesion to cells of the coating of the idealized microfluidic bifurcation, particle adhesion to proteins of the coating of the idealized microfluidic bifurcation, particle uptake by cells of the coating of the idealized microfluidic bifurcation, and combinations thereof.

6. The method of claim 2, wherein:

the coating of the idealized microfluidic bifurcation includes cells;

the liquid suspension of particles is introduced into the inlet of the microfluidic chip and caused to flow through the microfluidic chip at a specified shear rate of from 500 $sec^{-1}$ to 7.5 $sec^{-1}$;

the distribution of particles is determined by counting the number of particles adhered to the one or more locations of interest; and correlating the distribution of particles with one or more interactions is performed by determining % of cells in the one or more locations of interest that have taken up the particles.

7. The method of claim 1, wherein the one or more locations of interest consist of a middle of the parent channel, a middle of each of the one or more daughter channels, and the idealized microfluidic bifurcation.

8. The method of claim 7, comprising counting the particles interacting with the coating at the one or more locations of interest.

9. The method of claim 8, comprising plotting shear versus particles interacting with a specific location of interest for each of the locations of interest.

10. A method for characterizing one or more interactions between particles and a plurality of idealized microfluidic bifurcations comprising the steps of:

introducing a liquid suspension of particles into at least one inlet of a microfluidic chip, said microfluidic chip comprising a plurality of idealized microfluidic bifurcations, at least one inlet and at least one outlet wherein the microfluidic chip includes:

each idealized microfluidic bifurcation being a joint that fluidly couples a parent channel and two or more daughter channels that are in fluid communication with the at least one inlet and at least one outlet, one or more locations of interest that include each of the idealized microfluidic bifurcations having a well with a coating, the depth and width of each of each parent channel and daughter channel are between 10 micrometers and 500 micrometers, and the daughter channels of each idealized microfluidic bifurcation form an angle of between 15 degrees and 135 degrees at the idealized microfluidic bifurcation with respect to the parent channel; and the microfluidic chip comprises a symmetric idealized microfluidic bifurcation and an asymmetric idealized microfluidic bifurcation, or comprises an idealized microfluidic bifurcation fluidly coupled with daughter channels with the same cross-sectional areas and an idealized microfluidic bifurcation fluidly coupled with daughter channels with different cross-sectional areas;

causing the particle suspension to flow from the at least one inlet through the plurality of idealized microfluidic bifurcations to the at least one outlet such that at least a portion of the particles interact with the coating at the plurality of idealized microfluidic bifurcations;

measuring the particles that interact with the coating at the one or more locations of interest;

determining the distributions of particles on the coating at the one or more locations of interest with respect to the plurality of idealized microfluidic bifurcations; and correlating the distribution of particles with one or more interactions between the particles and the coating of the plurality of idealized microfluidic bifurcations.

11. The method of claim 10, wherein the plurality of idealized microfluidic bifurcations are arranged in parallel and are in fluid communication with a single inlet.

12. The method of claim 10, wherein the microfluidic chip comprises a single inlet and a single outlet and further comprises a plurality of idealized microfluidic junctions having the coating wherein:

the plurality of idealized microfluidic bifurcations and idealized microfluidic junctions form an idealized microfluidic network, the inlet is in fluid communication with the parent channel of a first idealized microfluidic bifurcation, the outlet is in fluid communication with the parent channel of a final idealized microfluidic junction, and the distribution of particles is determined on the coating of the plurality of idealized microfluidic bifurcations and junctions.

13. The method of claim 10, wherein the coating includes a substance selected from the group consisting of biological macromolecules, cells, and combinations thereof and the one or more interactions correlated with the distribution of particles includes an interaction between the particles and the substance.

14. The method of claim 10, wherein the particles are selected from the group consisting of prokaryotic cells, eukaryotic cells, liposomes, lipisomes, lipoproteins, microencapsulated drugs, particulate drug carriers, nanoparticles, microparticles, polymer beads, viruses, spores, and combinations thereof.

15. The method of claim 10, wherein the angles formed between the two or more daughter channels and the parent channel are not duplicated within the plurality of idealized microfluidic bifurcations.

16. The method of claim 10, wherein the ratios of the cross-sectional areas of the two or more daughter channels for each of the plurality of idealized microfluidic bifurcations is not duplicated.

17. The method of claim 10, wherein neither the angles formed between the daughter channels and the parent channel nor the ratios of the cross-sectional areas of the two or more daughter channels are duplicated.

18. The method of claim 10, wherein the one or more interactions between the particles and the coating of the plurality of idealized microfluidic bifurcations is selected from the group consisting of: particle adhesion to cells of the coating of the idealized microfluidic bifurcations, particle adhesion to protein of the coating of the idealized microfluidic bifurcations, particle uptake by cells of the coating of the idealized microfluidic bifurcations, and combinations thereof.

19. The method of claim 12, wherein the coating includes a substance selected from the group consisting of a substrate molecules, biological macromolecules, cells, and combinations thereof and the one or more interactions correlated with the distribution of particles includes an interaction between the particles and the substance.

20. The method of claim 13, wherein the fluid suspension of particles is introduced into the at least one inlet at decreasing shear rates of from 500 $sec^{-1}$ to 7.5 $sec^{-1}$ and further comprising the steps of determining counts of particles adhered at each of a number of the locations of interest and determining shear vs. the number of particles bound per unit area at the locations of interest.

* * * * *